(12) United States Patent
Baker et al.

(10) Patent No.: US 10,630,777 B2
(45) Date of Patent: Apr. 21, 2020

(54) TOPOLOGY FORMED BY ELECTRONIC NICOTINE DELIVERY DEVICES

(71) Applicant: Nicoventures Holdings Limited, London (GB)

(72) Inventors: Darryl Baker, London (GB); Ross Oldbury, London (GB)

(73) Assignee: Nicoventures Holdings Limited, London (GB)

(*) Notice: Subject to any disclaimer, the term of this patent is extended or adjusted under 35 U.S.C. 154(b) by 78 days.

(21) Appl. No.: 15/762,021

(22) PCT Filed: Sep. 21, 2016

(86) PCT No.: PCT/GB2016/052940
§ 371 (c)(1),
(2) Date: Mar. 21, 2018

(87) PCT Pub. No.: WO2017/051174
PCT Pub. Date: Mar. 30, 2017

(65) Prior Publication Data
US 2018/0270311 A1 Sep. 20, 2018

(30) Foreign Application Priority Data
Sep. 21, 2015 (GB) .................................. 1516674.7

(51) Int. Cl.
*H04L 29/06* (2006.01)
*H04L 29/08* (2006.01)
(Continued)

(52) U.S. Cl.
CPC .......... *H04L 67/125* (2013.01); *A24F 47/008* (2013.01); *A61M 11/042* (2014.02);
(Continued)

(58) Field of Classification Search
CPC ...................... A24F 47/002–008; A61M 15/06
See application file for complete search history.

(56) References Cited

U.S. PATENT DOCUMENTS 10,349,675 B2 * 7/2019 Choukroun ............ G16H 20/13
2004/0047319 A1 3/2004 Johannes
(Continued)

FOREIGN PATENT DOCUMENTS

CN 1633780 6/2005
CN 101800575 8/2010
(Continued)

OTHER PUBLICATIONS

IEEE Standard for Local Metropolitan Area Networks, Part 15.4: Low-Rate Wireless Personal Area Networks (LR-WPANs), IEEE Std 802.15.4, Sep. 5, 2011, 314 pages.
(Continued)

*Primary Examiner* — Thaddeus J Plecha
(74) *Attorney, Agent, or Firm* — Patterson Thuente Pedersen, P.A.

(57) ABSTRACT

The present disclosure teaches provision of a method that includes passing a data token from a first wirelessly connectable electronic nicotine delivery (END) device to a second wirelessly connectable END device. The method also includes using the token to control an aspect of the operation of a third wirelessly connectable device, the third wirelessly connectable device having an established communications relationship with the second wirelessly connectable END device.

21 Claims, 9 Drawing Sheets

(51) Int. Cl.
  *H04W 4/80* (2018.01)
  *A61M 15/06* (2006.01)
  *A24F 47/00* (2020.01)
  *A61M 11/04* (2006.01)
  *H04W 8/00* (2009.01)

(52) U.S. Cl.
  CPC ........... *A61M 15/06* (2013.01); *H04L 63/102* (2013.01); *H04W 4/80* (2018.02); *H04W 8/005* (2013.01); *A61M 2205/3546* (2013.01); *A61M 2205/3553* (2013.01); *A61M 2205/3561* (2013.01); *A61M 2205/3569* (2013.01); *A61M 2205/3592* (2013.01); *A61M 2205/3653* (2013.01); *A61M 2205/50* (2013.01); *A61M 2205/8206* (2013.01)

(56) References Cited

U.S. PATENT DOCUMENTS

| | | |
|---|---|---|
| 2011/0265806 A1 | 11/2011 | Alarcon |
| 2013/0276799 A1 | 10/2013 | Davidson |
| 2013/0284192 A1 | 10/2013 | Peleg |
| 2013/0340775 A1 | 12/2013 | Juster |
| 2014/0169599 A1 | 6/2014 | Solum |
| 2014/0174459 A1 | 6/2014 | Burstyn |
| 2014/0202477 A1 | 7/2014 | Qi |
| 2015/0099469 A1* | 4/2015 | Goldstein ............... H04W 4/21 455/41.2 |
| 2015/0224268 A1 | 8/2015 | Raymond |
| 2015/0327596 A1* | 11/2015 | Alarcon ............... A24F 47/008 131/328 |
| 2016/0363917 A1* | 12/2016 | Blackley ............... G05B 19/042 |
| 2017/0026905 A1 | 1/2017 | Denboer |
| 2017/0041868 A1 | 2/2017 | Palin |
| 2017/0273358 A1* | 9/2017 | Batista ................. A24F 47/008 |
| 2018/0132102 A1* | 5/2018 | Kwon ............... H04W 28/0215 |
| 2018/0280640 A1 | 10/2018 | Baker |
| 2018/0286208 A1 | 10/2018 | Baker |
| 2018/0303163 A1 | 10/2018 | Baker |

FOREIGN PATENT DOCUMENTS

| | | |
|---|---|---|
| CN | 102035574 | 4/2011 |
| CN | 102684753 | 9/2012 |
| CN | 103798960 | 5/2014 |
| CN | 203913385 | 11/2014 |
| CN | 104412629 | 3/2015 |
| CN | 1631013 | 6/2015 |
| CN | 104811895 | 7/2015 |
| EP | 1357712 | 10/2003 |
| EP | 1494403 | 9/2009 |
| EP | 2533477 | 3/2014 |
| JP | 2003229782 | 8/2003 |
| JP | 2005236819 | 9/2005 |
| JP | 2007036421 | 2/2007 |
| KR | 20020057207 | 7/2002 |
| RU | 2420901 C2 | 6/2011 |
| RU | 2011120430 A | 11/2012 |
| RU | 2536166 | 12/2014 |
| WO | WO 2005/057956 | 6/2005 |
| WO | WO14150704 A2 | 9/2014 |
| WO | WO2014195805 A2 | 12/2014 |
| WO | WO2015099751 | 7/2015 |

OTHER PUBLICATIONS

International Search Report and Written Opinion, International Application No. PCT/GB2016/052940, dated Dec. 8, 2016, 12 pages.
Great Britain Search Report, Application No. GB1516674.7, dated Feb. 18, 2016, 5 pages.
International Preliminary Report on Patentability, International Application No. PCT/GB2016/052940, dated Sep. 14, 2017, 8 pages.
Application and File History for U.S. Appl. No. 15/762,018, filed Mar. 21, 2018, Inventor: Baker.
Bronzi W et al., *Bluetooth Low Energy for Inter-Vehicular Communications*, 2014 IEEE Vehicular Networking Conference (VNC) IEEE, Dec. 3, 2014, pp. 215-221.
Yong Liu et al, *A Bluetooth Scatternet-Route Structure for Multihop Ad Hoc Networks*, IEEE Journal on Selected Areas in Communications, Feb. 1, 2003, vol. 21 No. 2, pp. 229-239.
Bluetooth, *Specification of the Bluetooth System: Experience More*, Specification vol. 1, Covered Core Package version: 4.0, Jun. 30, 2010, 137 pages.
Great Britain Partial Search Report, Application No. GB1516673.9, dated Feb. 18, 2016, 4 pages.
International Search Report and Written Opinion, Application No. PCT/GB2016/052939, dated Nov. 18, 2016, 17 pages.
International Preliminary Report on Patentability, Application No. PCT/GB2016/052939, dated Sep. 14, 2017, 9 pages.
European Office Action, Application No. 16775827.5, dated Jan. 28, 2019, 5 pages.
Japanese Office Action, Application No. 2018-513357, dated Jan. 29, 2019, 3 pages (7 pages with translation).
Russian Decision to Grant, Application No. 2018109578/08, dated Apr. 3, 2019, 12 pages.
Russian Decision to Grant, Application No. 2018109786/08, dated Dec. 13, 2018, 10 pages.
Russian Search Report, Application No. 2018109786/08, dated, dated Dec. 13, 2018, 2 pages.
Japanese Office Action, Application No. 2018-513274, dated Jan. 31, 2019, 2 pages (4 pages with translation).
Chinese Office Action, Application No. 201680047153.9, dated Nov. 21, 2019, 12 pages.

* cited by examiner

TOPOLOGY FORMED BY ELECTRONIC NICOTINE DELIVERY DEVICES

PRIORITY CLAIM

The present application is a National Phase entry of PCT Application No. PCT/GB2016/052940, filed Sep. 21, 2016, which claims priority from GB Patent Application No. 1516674.7, filed Sep. 21, 2015, each of which is hereby fully incorporated herein by reference.

TECHNICAL FIELD

The present disclosure relates to a topology and in particular but not exclusively to an approach for connecting electronic devices in a meshed or PICONET topology.

BACKGROUND

In conventional wireless communication approaches, such as Bluetooth and Bluetooth Low Energy (also known as Bluetooth Smart Technology), individual devices can be operated as nodes taking the role of masters or slaves in a particular communication relationship. Thus each node adopts the role of master or the role of slave. Accordingly, in a communication pair, one node acts as master and the other acts as slave. In the context of Bluetooth Low Energy, the master may be referred to as the central and the slave as the peripheral. One master (or central) node can be a master to several slaves (the exact number often limited by a particular chipset implementation) and although a node can be registered as a slave (or peripheral) to multiple masters, it can only be active as a slave to one master at any one time.

Bluetooth and Bluetooth Low Energy are fundamentally different in operation to other Low-rate wireless personal area networks (LR-WPANs) such as Zigbee™ and Thread™, which are both based upon the IEEE 802.15.4 wireless protocol.

Publications US2013/284192, US2014/174459, and US2011/265806 described examples of electronic cigarettes with a communication capability.

SUMMARY

Some specific aspects and embodiments are set out in the appended claims.

Viewed from a first aspect, there can be provided a wireless communication module, comprising: a wireless communication interface configured to operate at different times as a master device and as a slave device in separate communication relationships using the same communication protocol, wherein the interface is configured to switch back and forth between a master device mode and a slave device mode. Thereby the wireless communication module can form a mesh with other similarly configured modules, using a time-division approach to enable different modules in the mesh to take on different personalities in the mesh at different times.

Viewed from another aspect, there can be provided a wireless communication network comprising: a first and second wireless communication modules; wherein the first module operating in the slave device mode transmits advertising data representative of a data token to be transmitted across the network and the second module operating in the master device mode receives the advertising data transmitted by the first module, thereby to receive the data token; and wherein the second module operating in the slave device mode transmits advertising data representative of a data token to be transmitted across the network and the first module operating in the master device mode receives the advertising data transmitted by the second module, thereby to receive the data token. Thereby a meshing approach for inter-module communication can be achieved.

Viewed from a further aspect, there can be provided a method of transmitting data through a mesh network, the method comprising: at a first node of the mesh network adopting an advertising state in which a data token is included in first node advertising data transmitted by the first node; at a second node within wireless communication range of the first node and simultaneously with at least a portion of the duration of the advertising state at the first node, adopting a listening state in which the first node advertising data is received by the second node; at the second node and subsequent to receiving the first node advertising data, adopting an advertising state in which the data token received in the first node advertising data is included in second node advertising data transmitted by the second node. Thereby a time-shared meshing approach may be used to provide for communication between nodes in the network.

Viewed from another aspect, there can be provided a method comprising: passing a data token from a first wirelessly connectable device to a second wirelessly connectable device; and using the token to control an aspect of the operation of a third wirelessly connectable device the third wirelessly connectable device having an established communications relationship with the second wirelessly connectable device. Thereby an interaction between independent devices may be used to influence the behavior of a subsequent interaction between one of those devices and a third device.

Viewed from a further aspect, there can be provided a method of operating and aerosol provision device, the method comprising: operating a wireless communication interface of the device in a listening mode; during operation of the listening mode, receiving a data token from the wireless communication interface of another aerosol provision device; storing the received data token at the aerosol provision device; and providing the stored data token to an application operating device for control of an aspect of the operation the application operating device. Thereby the aerosol delivery devices may be configured to provide to interaction-influencing tokens to be transferred therebetween for passing on to an application device.

Viewed from another aspect, there can be provided an aerosol delivery device comprising: a wireless communication interface operable in a listening mode to receive a data token from the wireless communication interface of another aerosol provision device; and a data store operable to store the received data token; the wireless communication interface further operable to transmit the received data token to an application operating device having an operational association with the aerosol delivery device, for control of an aspect of the operation the application operating device. Thereby the aerosol delivery device may receive and store behavior-influencing data packets for later provision to an application device to enable an application to be executed with behavior that depends at least in part upon the behavior-influencing data packets.

Viewed from another aspect, there can be provided a method comprising: requesting from a wirelessly connected device a token stored at that connected device as a result of device-to-device interaction between the connected device and another device; receiving the requested token from the wirelessly connected device; providing the token to a remote service; receiving a profile from the remote service; and performing a comparison or interaction between the received profile and a profile associated with the wirelessly connected device. Thereby a device may carry out application functionality corresponding at least in part to a token stored by a connected device based upon a prior interaction by that connected device with another device.

BRIEF DESCRIPTION OF THE DRAWINGS

Embodiments of the present teachings will now be described, by way of example only, with reference to accompanying drawings, in which.

Figure 1:
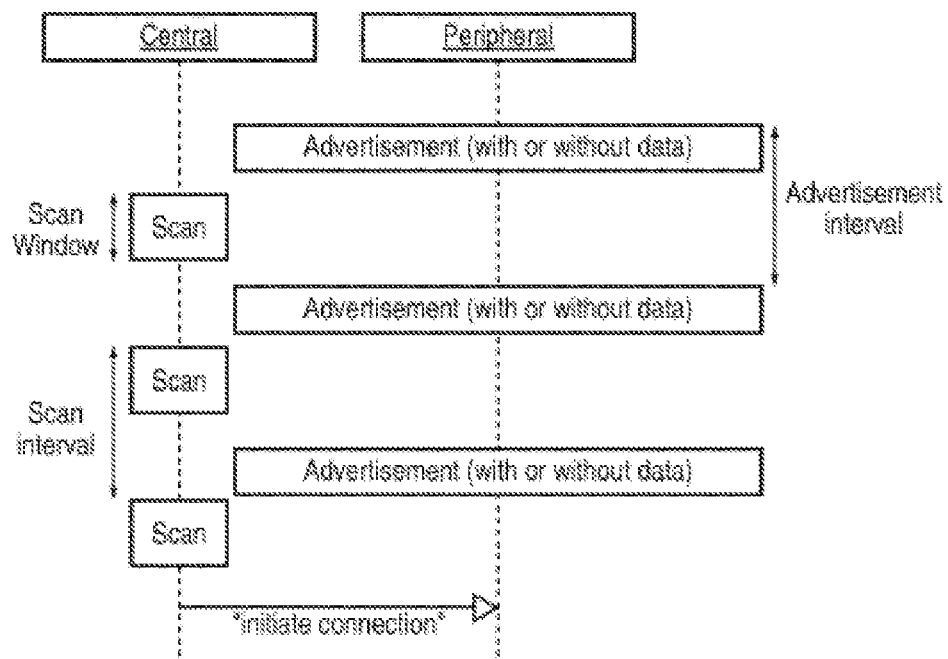
FIG. 1 schematically illustrates an advertising protocol.

While the presently described approach is susceptible to various modifications and alternative forms, specific embodiments are shown by way of example in the drawings and are herein described in detail. It should be understood, however, that drawings and detailed description thereto are not intended to limit the scope to the particular form disclosed, but on the contrary, the scope is to cover all modifications, equivalents and alternatives falling within the spirit and scope as defined by the appended claims.

DETAILED DESCRIPTION

The present disclosure relates to a modified form of wireless communication behavior. According to the present teachings, a device can be configured to use a Bluetooth or Bluetooth-like communications protocol and can, in a manner that may be transparent to other devices using the communications protocol for communication with the device, operate as both a master/central and a slave/peripheral in different communication relationships at the same time on a time division basis.

In some examples, the devices can be aerosol delivery devices such as so-called "E-cigarettes", sometimes also known as Electronic Nicotine Delivery devices (END devices), provided with electronics that allow them to communicate with other communication devices. In other examples, the devices may include electronic business cards or other portable devices that may have functionality related to an ability to interact in a mesh-type manner between multiple ones of those devices.

In the present examples, the devices use Bluetooth Low Energy ("BTLE"), but other Bluetooth protocols or Bluetooth-like protocols can take advantage of the present teachings. Bluetooth is a wireless technology standard for short distance communication between appropriately enabled devices. BTLE is a variant on the original Bluetooth system, designed to draw less power in use for extended battery life and/or small battery applications. Both Bluetooth and BTLE operate in the UHF radio industrial, scientific and medical (ISM) band from 2.4 to 2.485 GHz and are designed for creating so-called wireless personal area networks (PANs) for interconnecting devices over short distances. BTLE uses a modified version of the Bluetooth stack for communication such that a BTLE device and a traditional Bluetooth device are not directly compatible unless one device implements both protocols. Both Bluetooth and BTLE standards are maintained by the Bluetooth Special Interest Group (SIG). The present disclosure is provided in the context of a BTLE implementation using the part of the Bluetooth v4 specification that relates to BTLE. However, the skilled reader will appreciate that the present teachings can be applied to other Bluetooth approaches, such as the so-called Classic Bluetooth definitions that are also set out in the Bluetooth v4 specification. It will be further appreciated that the present teachings can be applied to technologies that are not in accordance with an entire Bluetooth specification, but which nevertheless behave in a Bluetooth-like manner.

For example, non-Bluetooth systems that nevertheless use an advertising setup based on the Bluetooth Low Energy Generic Access Profile (GAP) and thus have an advertising structure substantially as set out in FIG. 1 would be able to deploy the techniques of the present teachings. FIG. 1 illustrates an advertising structure according to which a peripheral (or slave or remote or secondary) device advertises its availability as a peripheral (or slave or remote or secondary) device during an advertisement period, with the advertisement periods being separated by an advertisement interval. The advertisement may include data for transmission, an indication that there is data for transmission or have no data reference at all. To receive the advertisement, a central (or primary or control) device scans for advertisements during a scan window. Multiple scan windows are separated by a scan interval. The relative duration of the scan and advertisement intervals is altered, either by determining that the interval at one device type is constant while the other varies, or by determining that both vary, which determination can be set by a standard or rule set for implementing the advertising protocol. By providing this relative variation in the scan and advertisement intervals, it is provided that even where an initial advertisement period does not overlap with an initial scan window, after a number of advertisement and scan intervals, an advertisement period will occur which overlaps with a scan window such that a connection can be initiated between the central and the peripheral device.

Figure 2:
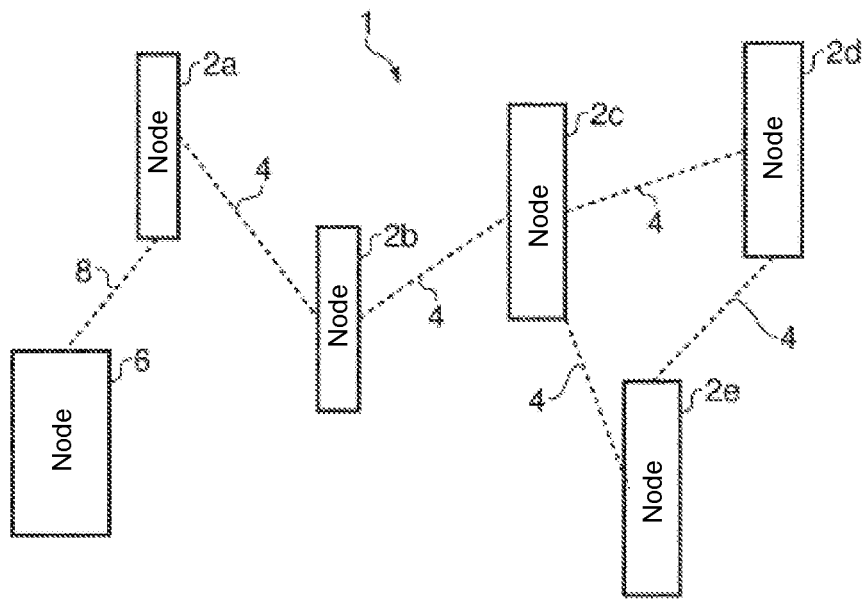
FIG. 2 schematically illustrates an example devices environment.

A first example of a devices environment 1 in which the present teachings can be utilized is shown in FIG. 2. In this example, a number of nodes 2a through 2e are present in the devices environment 1. Various of the nodes 2 are interconnected via wireless links illustrated by dotted lines 4. However, not every node 2 is directly interconnected with each other node. Rather, the nodes 2 are interconnected in a mesh-like pattern with a scatter net data flow. Thus, it can be seen that for a message to pass from node 2a to node 2d, that message would be passed via nodes 2b and 2c (and optionally also 2e) in order to reach node 2d. From some perspectives, it may be considered appropriate to describe these interactions as a PICONET as an alternative to using the description of meshing or meshed interaction. To provide for ease of readability this description will use the term mesh throughout.

To achieve such a mesh-like communication structure, a device consistent with the present teachings can take on more than one persona and thus can belong to more than one BTLE communication relationship and furthermore, the device can act as a central or a peripheral in one BTLE communication relationship and as a peripheral in another BTLE communication relationship. To manage the simultaneous nature of these different personas, the device of the present teachings can be operated to switch between the two personas, such that at any one time the device adopts only one persona. The switching back and forth between personas happens often enough that each communication relationship is maintained without the devices with which those communication relationships are formed concluding that the device has become unavailable and closing those communication relationships.

Switching between the personas within a given device would take place on a timescale consistent with the demands a particular application for the device. There is some random element to the switching, as illustrated with respect to FIG. 1 above. The time ranges within which the random element can operate would however be set in accordance with application demands. For example, to provide for rapid data transmission through a mesh of devices the persona switching would occur at relatively high frequency. For example in an implementation based upon interactions by devices associated with users in a transient location (such as where the devices are electronic business cards in a networking meeting or are END devices in a social situation) then each device may be configured to switch roles every few seconds. On the other hand, for greater power efficiency and where data transmission speed through the mesh is of lower concern a relatively lower persona switching frequency can be used, perhaps dropping in a suitable context to switching roles only once or twice per hour. Also, the relative duration of peripheral and central roles can be altered according to the factors applicable to the implementation environment. Thus while the central persona is active the device will send data as part of the advertising packet, and while the peripheral persona is active the device will listen for devices advertising data packets.

Additionally, a device according to the present teachings can have multiple central personas, which can be used to communicate in different meshes or to increase the total number of peripherals with which it can hold bond relationships at any one time above a limit imposed by the particular Bluetooth chipset deployed. These multiple central personas can be implemented by using the persona switching approach outlined above, or by implementing multiple BTLE MCUs.

By using such a technique, for example, the interconnections between the nodes 2 could occur in the form of node 2a acting as central and node 2b acting as peripheral in a first BTLE relationship. Node 2b may also act a central in a second BTLE relationship that features node 2c as a peripheral. Node 2c may in turn be the central in a third BTLE relationship that includes nodes 2d and 2e as peripherals. Further, node 2d may be also be central in a fourth BTLE relationship that includes node 2e as a peripheral. As will be appreciated, other orderings of which nodes function as central and peripheral in various possible node relationships can be implemented. For example, the connectivity shown in FIG. 1 could alternatively be provided by having node 2b function as central in a BTLE relationship in which nodes 2a and 2c are peripherals, and by having node 2d function as central in a relationship in which node 2c is a peripheral, and by having node 2e function as central in a relationship in which nodes 2c and 2d are peripherals. As will be seen from the discussion below, the arrangement of relationships to make up the mesh may be determined on an ad-hoc basis depending upon which nodes become centrals as a result of the relationship establishment process.

The mesh approach set out in the present disclosure allows the passing of small data packets or tokens between nodes without a need to establish full BTLE bond relationships between the nodes. Thus such tokens may be flooded through a mesh of any two or more nodes based upon transient or impermanent node to node relationships where the peripheral to central relationship lasts just long enough to transmit and receive the token. This approach does not prevent some or all of the nodes in the mesh establishing bond relationships (also known as pairing). Such a bond-based approach may be used for example in circumstances where volumes of data larger than can be accommodated using tokens need to be transmitted between nodes in the mesh.

As also illustrated in FIG. 2, an additional node 6 may be provided. The node 6 need have no knowledge or capability in respect of the meshable interconnectivity of the nodes 2 and instead implements the communication protocol in a conventional way. Thus, in the present example, the node 6 implements a conventional BTLE interface and is able therefore to establish a connection 8 with one of the meshable nodes 2 such that the node 6 acts as central and the node 2 acts as periphery.

Accordingly, it will be seen that the approach of the present teachings allows a Bluetooth or BTLE-based mesh to be established without a controlling device that provides a core node for a star-type topology. The mesh can interact with a non-meshed device, but this interaction can be either continuous or intermittent and the non-meshed device need not have any role in establishing, controlling or configuring the mesh.

Therefore, by establishing such a mesh network, the various nodes 2 can communicate with each other and pass information on to other nodes within range using an existing communication protocol such as BTLE. However, as will be appreciated from the discussion, the node uses a modified form of the Bluetooth hardware implementation with Generic Attribute Profile (GATT) Notification to achieve this ad-hoc meshable behavior. As will be appreciated from the present teachings, this modification can be achieved by implementing a modified hardware, firmware or software implementation of the protocol, for example by using an implementation of a controller circuit that complies in many respects with the standard communication protocol, but includes additional functionality provided for example using a script to achieve the device-to-device interactions described herein. The additional functionality may be introduced using modified hardware which, while this involves using non-standard hardware, does provide that the hardware could provide both modes on a full time basis without the need for time-divided sharing of the personas. The controller circuit may be a hardware circuit with functionality provided by its configuration, such as an application specific integrated circuit (ASIC) or may be a programmable microprocessor (g) or microcontroller (MCU) operating under firmware and/or software control.

Figure 3:
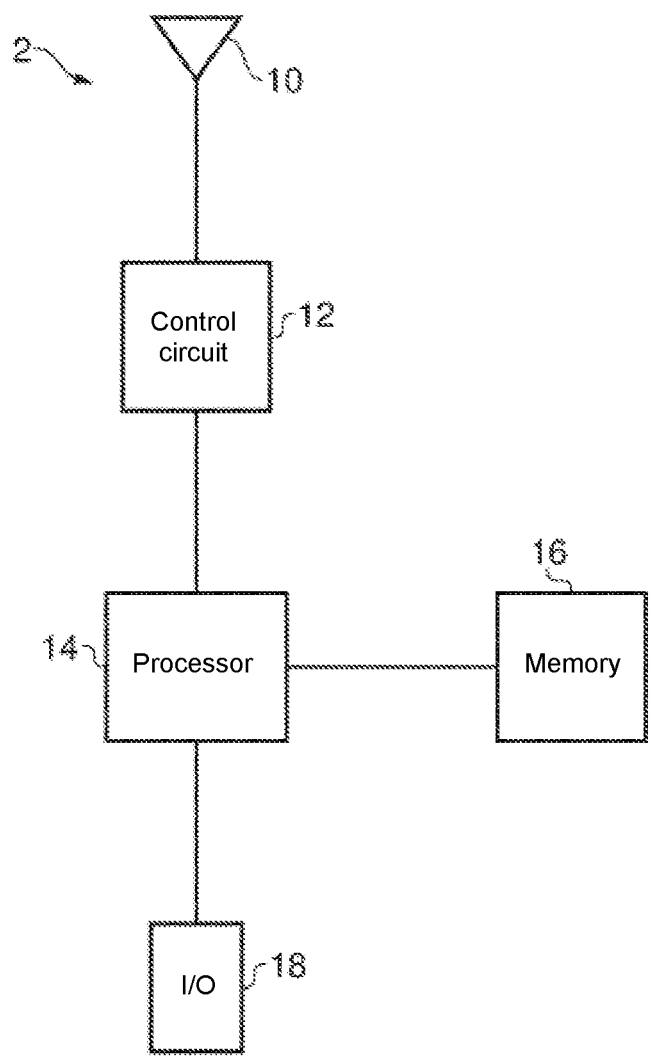
FIG. 3 schematically illustrates functional components of a node.

FIG. 3 illustrates schematically the functional components of each node 2. Each node 2 has an antenna 10 for transmitting and receiving BTLE signals. The antenna 10 is connected to a BTLE control circuit 12 such as a BTLE MCU. The control circuit 12 receives data for transmission from and provides received data to a device core functionality processor 14 which operates, for example in conjunction with memory 16 and/or I/O elements 18 to carry out the core computing functionality of the node 2. Although it has been shown in FIG. 3 that the functional components of the node 2 interact on an direct link basis, it will be understood that as FIG. 3 is schematic in nature, this description also includes alternative arrangements of the functional components, for example on a bus interconnect basis. It will also be appreciated that one or more of the functional components illustrated may be provided by a single physical component, and also that one functional component may be provided by multiple physical components.

With regard to the functional components relating to the core computing functionality of the node 2, it will be appreciated that the nature and usage of these components may differ depending upon the nature of the device itself. In the example of the device corresponding to a particular node being an electronic business card, the core computing functionality may include providing storage, display and transmission control options for business card information along with transmission and reception of such information (which would be carried out using the control circuit 12 and antenna 10). In the example of the device corresponding to the node 2 being an END device, the core computing functionality may include passing or information tokens between END devices, monitoring and reporting of device charge and/or nicotine fluid levels, lost and found interactions, and usage recording. Thus it will also be appreciated that the core computing functionality may differ from a user-perceived core functionality of the device. For example, in the case of an END device, the user-perceived core functionality will likely be that of aerosol generation for nicotine delivery, with the computing functionalities being additional, supplementary or secondary to that user-perceived core functionality.

Figure 4:
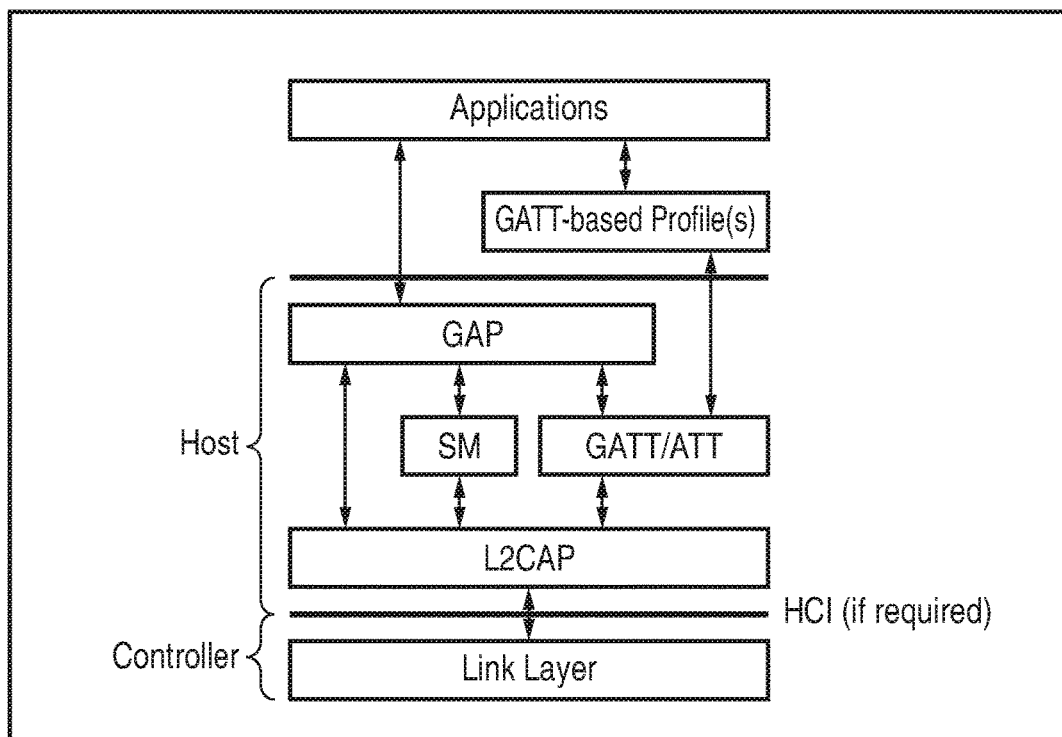
FIG. 4 schematically illustrates a protocol stack.

FIG. 4 then illustrates schematically a protocol structure as implemented by the control circuit of each node 2. The protocol structure illustrated in FIG. 4 corresponds to the Bluetooth stack, which includes the GATT (generic attribute protocol), GAP (generic access protocol), SM (service manager protocol), GATT/ATT (low energy attribute protocol), L2CAP (logical link control and adaptation layer), and link layer. In the present examples the link layer operates on a LERF (low energy radio frequency) basis. As illustrated in FIG. 4, the protocol stack can be conceptually divided between the so-called Host and Controller layers. The controller part is made up of the lower layers that are required for physical layer packets and associated timing. The controller part of the stack may be implemented in the form of an integrated circuit such as a SoC (system-on-a-chip) package with an integrated Bluetooth radio.

The layer implementations relevant to understanding the present teachings include the link layer, the L2CAP, the GAP and the low energy attribute protocol.

The link layer controller is responsible for low level communication over a physical interface. It manages the sequence and timing of transmitted and received frames, and using link layer protocol, communicates with other nodes regarding connection parameters and data flow control. It also handles frames received and transmitted while the device is in advertising or scanner modes. The link layer controller also provides gate keeping functionality to limit exposure and data exchange with other devices. If filtering is configured, the link layer controller maintains a "white list" of allowed devices and will ignore all requests for data exchange or advertising information from others. As well as providing security functionality, this can also help manage power consumption. The link layer controller uses a host controller interface (HCI) to communicate with upper layers of the stack if the layer implementations are not co-located.

The logical link control and adaptation layer protocol (L2CAP) component provides data services to upper layer protocols like security manager protocol and attribute protocol. It is responsible for protocol multiplexing and data segmentation into small enough packets for the link layer controller, and de-multiplexing and reassembly operation on the other end. The L2CAP's has a backend interface is for the GAP that defines the generic procedures related to the discovery of BTLE devices and link management aspects of connecting to other BTLE devices. The GAP provides an interface for the application to configure and enables different modes of operation, e.g. advertising or scanning, and also to initiate, establish, and manage connection with other devices. The GAP is therefore used control connections and advertising in Bluetooth. GAP controls device visibility and determines how two devices can (or cannot) interact with each other.

The low energy attribute protocol (ATT) is optimized for small packet sizes used in Bluetooth low energy and allows an attribute server to expose a set of attributes and their associated values to an attribute client. These attributes can be discovered, read, and written by peer devices. The GATT provides a framework for using ATT.

As will be apparent from the discussions above, the present teachings use the advertising process to facilitate the meshed interaction of multiple devices, for example to permit scattering information between an unlimited number of devices for the purpose of disseminating data over distances and time.

Figure 5:
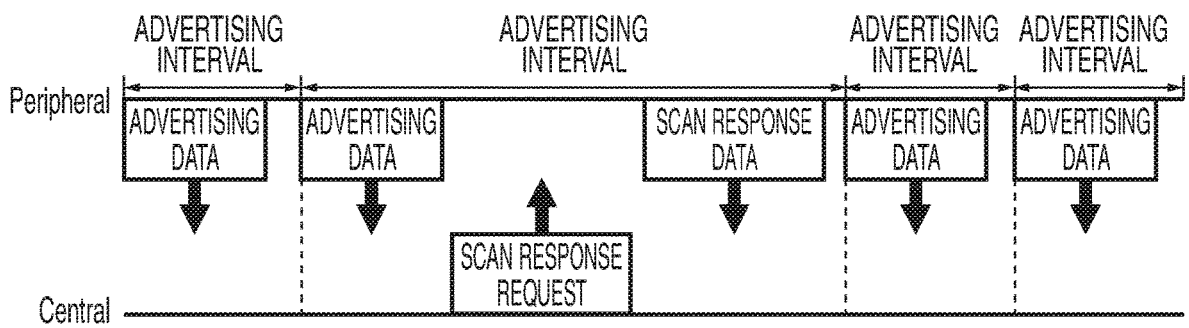
FIG. 5 schematically illustrates scan response timing.

In the context of the present examples, an application running on a device communicating via the meshed structure described herein may request or watch for specific scan response payloads, responsive to a scan response being sent by that device. This approach is used in conventional Bluetooth implementations to transmit the device name and other identification details. However in the present approaches, this scan response, which is defined as a 31 byte data packet, also referred to as a token, is used to share ID information related to a variable that when read by an application will trigger a particular response or action. The timing of such requests is illustrated in FIG. 5. As can be seen from this Figure, the scan response request is transmitted by the central device during the advertising interval and the scan response data is provided by the peripheral before the start of the next advertising interval.

By implementing the approach of the present teachings, data passing over the physical layer is indistinguishable at that level from ordinary BTLE traffic. Also, although higher-level layers are modified to accept the present meshable-interaction of devices, a non-meshable enabled application can communicate over BTLE using a device consistent with the present teachings.

Also, a device that utilizes only a conventional BTLE stack (such as node 6 illustrated in FIG. 2 above) can communicate with a device 2 that uses the meshable approach of the present teachings. The conventional BTLE device can then receive data from the meshable device 2 without the BTLE stack in the conventional BTLE device having any knowledge of the meshed interactions of the devices 2. The data that the conventional BTLE device receives may have originated at the directly connected device 2, or may have originated at another device that previously connected to the directly connected device 2 via the mesh and which data has been stored or cached at the meshable device 2. The origin of such mesh-transferred data could be another meshed device 2, or could be another conventional BTLE device that is or has been connected to a meshed device.

Figure 6:
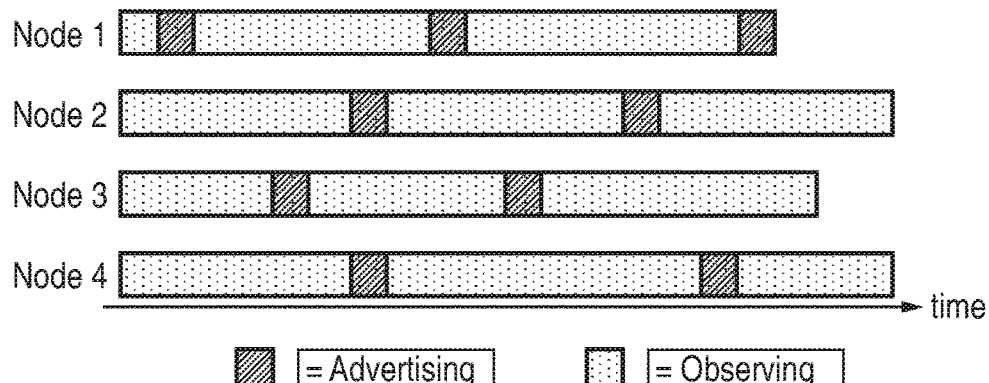
FIG. 6 schematically illustrates mode scheduling.

FIG. 6 illustrates schematically the behavior of each node 2 in relation to managing the dual persona nature of each node 2 to establish connections as both central and peripheral. As BTLE provides for two operating modes at the presentation layer, one corresponding to each of central and periphery roles, the node 2 of the present examples alternates between these two modes so as to provide for both advertiser broadcasting to advertise its capability as a peripheral and for observer activity to look for other peripheral-capable nodes to which it can connect as central. While acting as observer, the node can act upon any received broadcaster advertisement to establish a connection as central in accordance with the usual BTLE conduct, for example as set out in the BTLE Generic Access Profile (GAP). While performing advertiser broadcasting, it will be able to establish a connection as peripheral with an observing node that responds to become a central. As is discussed above, this time-sharing between the personas of central and peripheral carries on after the connections between the devices have been established. This provides that the single device can operate in both modes on an ongoing, albeit time multiplexed, basis based upon a single BTLE MCU in the device.

Thus a device (node) configured to provide the meshable-interaction of the present example uses the standard BTLE GATT (Generic Attribute Profile) specification in combination with a modified GAP to adopt the two operation modes associated with the dual-persona nature of the node. As will be discussed below, the node alternates between advertising as a peripheral and listening as a central so as to facilitate being able to connect to other nodes in both central and peripheral modes. Typically the device already has an indication of the identity of the mesh in that the devices can be pre-programmed to use a particular UUID tied to the particular device mesh ("service" in BTLE terms) that the devices are intended to participate in. For example all electronic business card devices may be programmed to use the same UUID and likewise all END devices from a particular brand, range, or manufacturer may be programmed to use the same UUID. Within this context, to identify the active persona or mode, the node uses a node ID code that uniquely identifies the node within the mesh. The node ID and UUID (in effect mesh ID or group ID) codes are held in the firmware of the device and inserted into the advertising packets along with the data that makes up the token and may also be referenced in scan response requests and scan response messages as part of the advertising under GAP interactions with and between the devices.

While operating as a central, the node can adopt the states Scanner, Initiator and Master, and while operating as a peripheral the node can adopt the states Advertiser and Slave.

FIG. 6 also illustrates the relative advertising and observing times of multiple nodes. The illustrated approach tends to avoid (but not necessarily exclude) multiple nodes in range of one another performing broadcast simultaneously. In the present example, the duration of the observing period is controlled to fall in the range of 0.01 ms and 5 s, and the advertising period is of a fixed duration which may be in the range of 0.5 s to 10 s. In other examples, the advertising duration may also be variable and the observing duration may fall within a different range, overlapping range or subset of the example range given above. Such time offsetting can be achieved in a number of ways such as by coordination between the nodes, or by each node using an interval length adjustment such as to provide uneven time spacing between each mode transition. Such interval length adjustments could be provided by selecting for each interval one of a number of possible interval lengths or by using some form of interval duration randomizer.

When a node is observing with a view to establishing a role as a central in a mesh, the node acts no differently to a node with no meshing capability when listening for advertisement from a potential peripheral node. Thus a node operating in this mode can also become a central to a conventional BTLE device without the meshing capability of the present teachings.

When a node is advertising with a view to establishing a role as a peripheral in a mesh, it advertises using a structure based upon the BTLE GAP data. However the BTLE GAP structure is modified to include mesh-specific information that can be recognized by a mesh-capable device which receives the advertisement. The mesh-specific information can include fields such as:
 the node ID of the advertising node;
 packet sequence number of a packet awaiting transmission from that node, this is used to avoid duplicates—depending on the application, this may simply be a packet sequence of packets originated from that node (for example where the application requires only that the payload or token from the advertising node is flooded to multiple other nodes) but could be made unique for a given mesh (group ID), time window and/or other uniqueness scope according to the application requirements;
 source node identifier of the packet having that packet sequence number, to reflect that the token now being passed may have originated at a different node to the one that is now passing it on;
 destination node identifier for the packet having that packet sequence number, depending on the implementation this can be an single node (corresponding to some form of routed operation) or 'all' nodes (corresponding to flooding type operation);
 the group ID of the source node for the packet having that sequence number, which is used to allow multiple mesh networks to co-exist in the same physical space (as explained above, this group ID typically uses the BTLE UUID, although another group ID filed could be defined and used if required);
 life time or expiry time of the packet having that sequence number payload, the data specific to a particular application—for example data relating to an electronic business card or END device application.

In accordance with the BTLE data handling approach, if a given application payload item is too large for a single packet, that payload item is broken down and distributed within multiple packets before reassembly at the/each destination node. In such applications a bond may be established between nodes so as to provide for more transmission management for this larger data volume.

Figure 7:
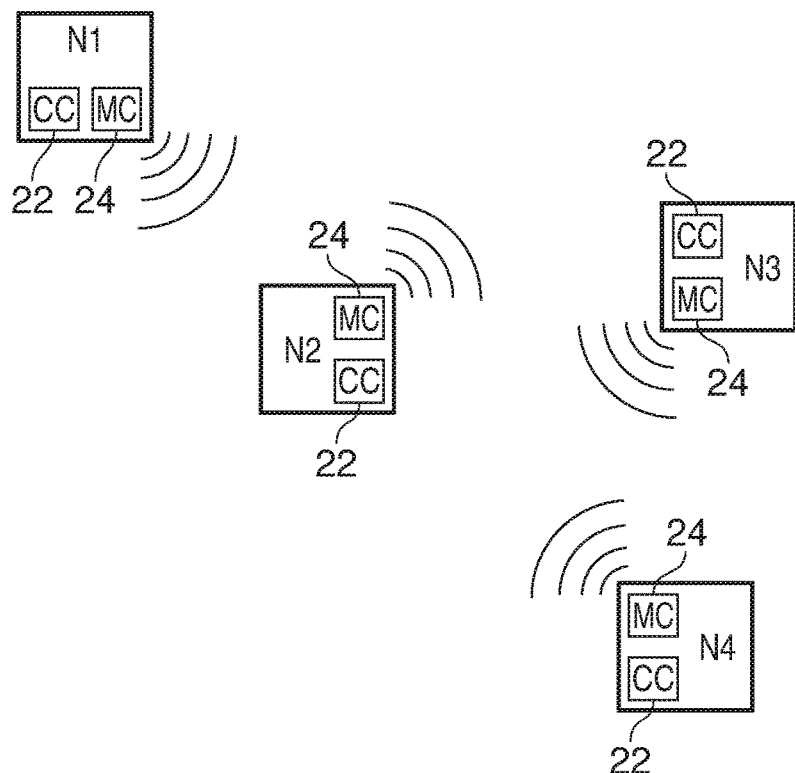
FIG. 7 schematically illustrates a mesh of nodes.

FIG. 7 schematically illustrates connectivity patterns between a number of nodes N1, N2, N3 and N4. In this illustration, node N1 is out of range for direct communication with node N4. Different operation modes of the nodes are signified by the elements control chip (CC) 22 and mesh chip (MC) 24 of each of nodes N1 to N4. The control chip is representative of the node MCU operating to communicate with a conventional BTLE device such as the device 6 shown in FIG. 2. The mesh chip is representative of the node MCU operating in both central and peripheral modes to communicate through the mesh.

In the example of FIG. 7, node N1 has a bit set in an advertisement data field indicating that it has data to send. The schedule of advertising and observing in each nodes causes node N2 to be the first node in direct communication range with N1 to listen as a central following node N1 having the advertisement data field set. Thus node N2 when in central mode receives the advertising data which N1 is advertising while in peripheral mode. This advertising data, as received by N2 can be used by N2 in connection with an application running at or otherwise associated with N2. In addition or alternatively, node N2 can cache the advertising data ready for onward transmission as advertising data on a future occasion that node N2 adopts its peripheral persona. Thereby, the advertising data that originated at N1 can pass onward from N2 as advertising data that it then received by node N3 at a time when N2 is advertising as peripheral and N3 is listening as central. The advertising data that originated with N1 can then be used and/or passed on by N3, ultimately arriving at N4 by the same method.

It should be noted that in this implementation, the advertising data is effectively flooded across the mesh. Thus, if N1 happens to be listening as central at the same time that N2 is advertising as peripheral, the advertising data will return to N1 as well as passing onward through the mesh to N3. In this circumstance either the node N1 or some application running at or associated with N1 may simply discard the returning advertising data. In some implementations, the node or application may make use of the returned advertising data in some way, for example using the time between transmission and receipt as some form of random interval generator or for mesh diagnostics.

As has been explained above, it is possible for the transmission over the mesh to be in the more structured format of using established bonds between the nodes. In such a circumstance, each pair of nodes will interact over an established bond and the persona switching at each node will provide for data received in a bond of which one persona is a member can then be onwardly transmitted using a bond of which the other persona is a member.

Control as to whether the data is transmitted to every node (flooding) or whether the data is transmitted only to selected nodes (routing) can be achieved in several ways. If the data is to be automatically communicated to all nodes without restriction, then this can be a default state configured into the nodes. If the data is to be transmitted only to nodes currently active in the mesh, then this can be achieved either as default behavior set in the nodes or on an application-specific basis where the application is mesh-aware and provides control information to the communication stack to indicate the data transmission extent. If the data is only to be transmitted to specific nodes, this can be achieved on an application-specific basis where the application is mesh-aware and provides control information to the communication stack to indicate the data transmission extent. The present examples are configured to operate on the basis of a flooding approach such that data is automatically forwarded to all presently-meshed devices.

Figure 8:
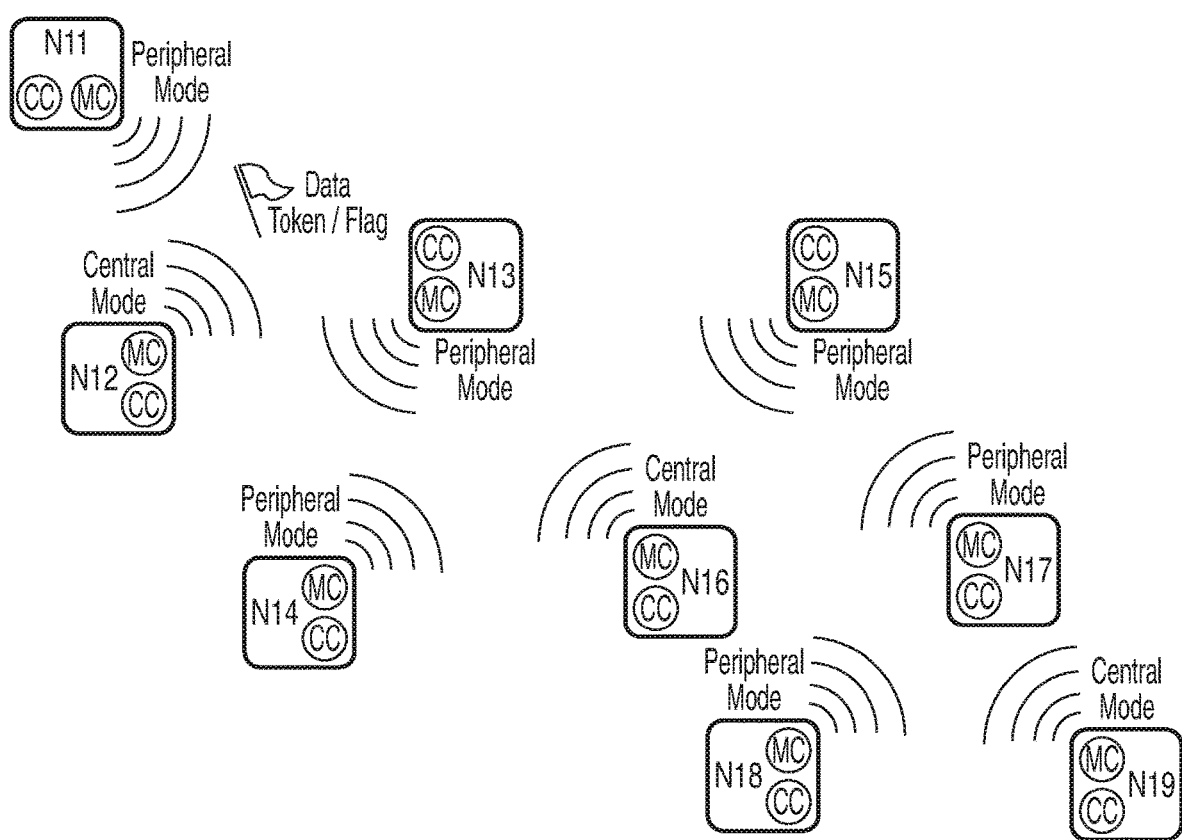
FIG. 8 schematically illustrates a mesh of nodes.

FIG. 8 provides a further illustration of meshing behavior as between nodes. In this example, a larger number of nodes N11 to N19 are present. The illustration in FIG. 8 represents a given snapshot in time such that different ones of the nodes are illustrated as having currently adopted different ones of their respective peripheral and central personas. At the time illustrated in FIG. 8 three nodes have become configured into central mode, these being nodes N12, N16 and N19, with the remaining nodes having become configured into peripheral mode. As will be appreciated from the discussion above, for any given instance of the same nodes being present in the same locations, the exact number and identify of the nodes that become configured into the central mode will depend upon factors such as the scheduling by each node of its advertising/observing periods and the relative location of each node compared to any other node that has already become configured into either central or peripheral mode. The passing of a data token is illustrated in the figure by the presence of a flag passing from N11 sending this data token in its advertising data to N12 which will receive that advertising data listening in central mode. This token will later be included in advertising data from N12 when N12 adopts its peripheral persona. Thereby the token can be passed onward through the mesh and ultimately arrive at each node in the mesh at least once.

As will be understood from the discussion above, the meshes can change dynamically based upon changes to the numbers and positions of nodes in the mesh. For example as nodes move away from the remainder of the mesh, eventually they will lose contact with all nodes in the mesh and leave the mesh. Likewise, a node that is deactivated or enters a power saving non-wireless mode will lose contact with the other nodes in the mesh and leave the mesh. Further, new nodes not previously a part of the mesh will be able to join the mesh as and when they come within range of a node in the mesh or when they are powered while within range of a node in the mesh. Also, as will be understood from the discussion of persona switching above, a node already within the mesh and operating as a peripheral within the mesh will also operate at a different time as a central within the mesh. In an implementation in which the mesh adopts bond relationships such that particular nodes have defined roles as centrals in some bonds and peripherals in others, if a node then changes location relative to the nodes in the mesh it may in effect leave the mesh as all established bonds may cease to operate of the range to the new location. Such a node would then resume attempting both observing and advertising until it establishes one or more new bond relationships into other nodes of the bond-linked mesh.

As the skilled reader will appreciate, Bluetooth and BTLE provide for securing of an inter-node communication bond. This is not applicable to the purely advertising-based transmission of tokens in the form of advertising data unless such transmission of tokens leads to the establishment of bond relationships. In the present examples, even where bond relationships are used, the nodes can be configured to establish such bonds without requiring user input to confirm trust between the different nodes or devices. Rather, in the present examples, devices or nodes of a particular type can be configured to pre-trust all other devices or nodes of that particular type. For example, in the case of the devices being electronic business cards, each electronic business card can be configured to trust all other devices that identify as being electronic business cards from a given manufacturer, group of manufacturers, brand, group of brands, model, group of models or as being compliant with a given electronic business card standard or group of standards. In the case of the nodes being END devices, each END device can be configured to trust all other devices that identify as being END devices from a given manufacturer, group of manufacturers, brand, group of brands, model, group of models or as being compliant with a given END device standard or group of standards.

Such a trust pattern can be supplemented with inherent controls on the amount of personal data that the device stores/is permitted to transmit. For example, an END device may be configured by the owning user to not hold or to be prevented from sharing any information that identifies the owner. This would not preclude the END device from interacting with other END devices to pass on information that can be used for lost/found functionality or from passing on information about the END device itself to provide for group interactions between END devices of the same brand or model, for example as discussed below. In the example of an electronic business card, the user could limit the device to holding or being permitted to share only information that is otherwise possible to find publicly such as name and business contact details or social mobile platform address of the user. A social mobile platform address could take the form of a link to the user's profile on a social networking platform such as LinkedIn™ or other business social networking platform. Also, a user of an electronic business card may choose to activate the device only at selected times, such as when attending a professional education event or networking event, thereby to prevent the electronic business card from sharing information with any compatible electronic business card that may be present at other locations, such as on a bus or other public transport.

In other examples, trust may be a user-explicit functionality, such that a user may be required to actively accept or request a communication bond to be established with another node.

Where a particular node or device is being configured by the user, for example to communicate with a conventional BTLE device of the user such as a smartphone, phablet or tablet device, the trust relationship between the user's meshable device and conventional BTLE device may be secured in the same manner as other conventional BTLE pairings to establish a communication bond.

Thus it will be understood that by using the approach of the present teachings, a device can be provided that is capable of meshed interaction with other similar devices by adopting a dual-persona structure in which the device is able to operate on a time-division basis as both a master (central) and slave (peripheral) for communication with those other like devices while also operating as a slave/peripheral to a conventional device without the dual persona capability.

This approach can be used to facilitate device-to-device interactions between a range of devices for a range of purposes. As discussed above, examples of devices that can be equipped for such device-to-device interactions using the meshed or PICONET topology approach of the above examples include electronic business cards and electronic nicotine delivery devices (END devices).

Figure 9:
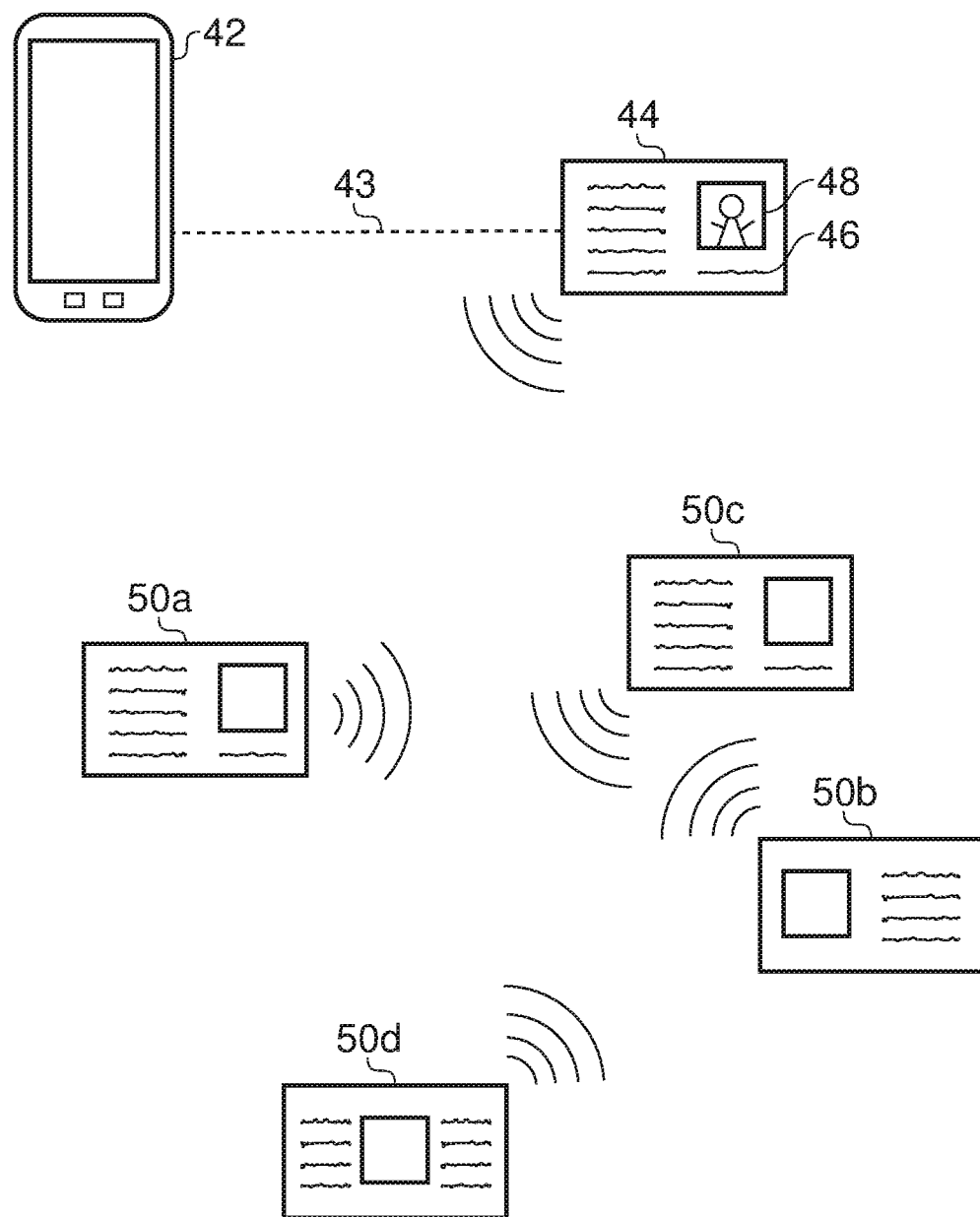
FIG. 9 schematically illustrates an example implementation of a meshed node topology.
Figure 10:
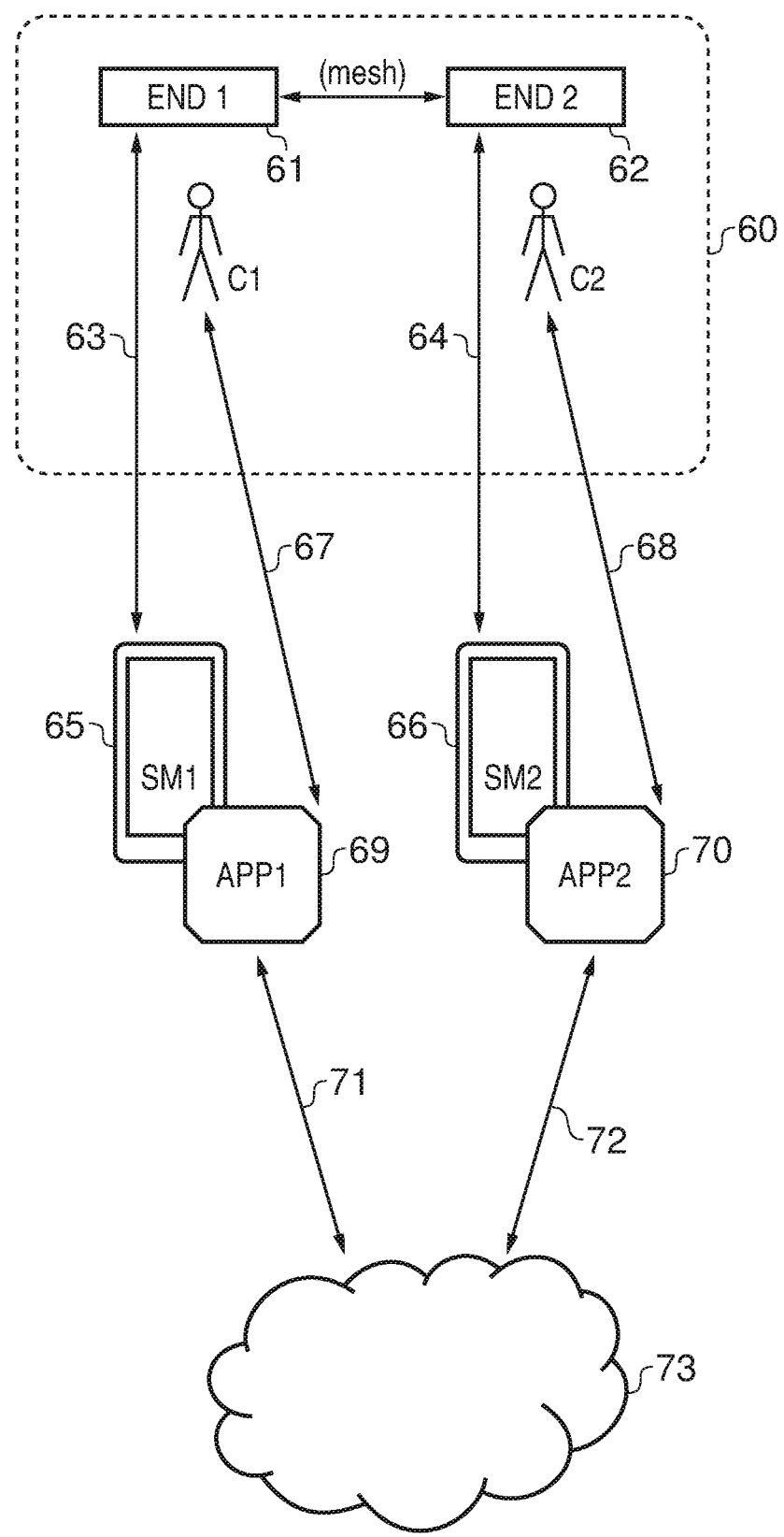
FIG. 10 schematically illustrates an example arrangement for device-to-device interaction using meshing approach.

With reference to FIG. 9, there will now be discussed a first example of a system implemented using the meshing devices approach of the present teachings. As shown in FIG. 9, a user device 42, such as a smartphone, phablet or tablet has a communication relationship (illustrated by dashed line 43) with an electronic business card device 44. The electronic business card device 44 may include one or more visible representations thereon to identify the device as an electronic business card and/or to provide written 46 and/or photographic 48 details of the user of the electronic business card. In some examples, the electronic business card device 44 may be provided with an electronic display on which the visible representations may be selectively displayed depending upon an operational parameter or power state of the electronic business card device 44.

The electronic business card device 44 also has a wireless communication capability for meshed interaction between nodes, consistent with the teachings set out above. Thus, in the present example, the electronic business card device 44 has a BTLE capability enabling communication with both conventional BTLE devices and mesh-capable BTLE devices.

The user device 42 of the present examples has a conventional BTLE capability, such that the user device 42 and the electronic business card device 44 can establish a BTLE pair-bond communication relationship as the communication relationship 43. The user of the user device 42 can change data and/or operational parameters of the electronic business card device 44 via the communication relationship 43. Thus the user of the user device 42 can set the electronic business card device 44 to store business contact information of the user. Such business contact information may include any one or more of name, company, field of business, contact details, and link/address of a user profile on a social media platform. Examples of social media platforms which could be referenced in such a link or address include professional networking oriented social media platforms such as LinkedIn™ or ReseachGate™, and general use social media platforms such as Facebook™, Instagram™, Twitter™, VK™ or Qzone™.

In the present example, the electronic business card device 44 is programmed with a user name, a user company name and a link to the user's social media profile. Also, the user's electronic business card device 44 is programmed to communicate with other electronic business card devices only when in an active state. The active state can be triggered by either or both of a physical switch on the electronic business card device 44 or a command transmitted to the electronic business card device 44 from the user device 42 via the communication relationship 43. The electronic business card device 44 is operable in the active state whether or not the communication relationship 43 is active. Thus the user can turn off a BTLE function of the user device 42 or separate the user device 42 from the electronic business card device 44 without affecting the ability of the electronic business card device 44 to operate.

When the electronic business card device 44 is, while in the active state, within BTLE communication range of other trusted electronic business card devices, it will be able to establish communication relationships using the meshing functionality in order to communicate with those other electronic business card devices. This is illustrated in FIG. 9 by the additional electronic business card devices 50a to 50d. The establishment of roles within the mesh of electronic business card devices 44 and 50a-d will depend upon the relative advertising schedules of the individual devices. However, in some combination, the electronic business card devices 44 and 50a-d will establish a mesh communication between one another and will be able to exchange data according to the business card functionality of the applications programmed into the electronic business card devices.

Accordingly, through action of the electronic business card application functionality, the electronic business card device 44 will be able to communicate its user business data to the other electronic business card devices 50a-d and will be able to receive respective user business data from each of the other electronic business card devices 50a-d. This received user business data can be stored by the electronic business card device 44 until the electronic business card device 44 next activates the communication relationship 43 with the user device 42.

Once the electronic business card device 44 has communicated with the user device 22 to pass the stored user business data to the user device, a business data receiving application of the user device 22 can be used to view the data. In the present example, where the stored business data includes a respective link to a social media profile of the user whose business card provided the data, it the business data receiving application may provide for the link to be followed to enable the user of the other device 42 to view the profile of that other user and optionally invite that other user to connect using that social media platform.

Thus it will be appreciated that the meshing technology discussed herein may have a number of uses to facilitate communication with other meshed devices while also being capable of communicating directly with a user device without meshing capability, such as a smartphone, phablet, tablet, laptop computer, netbook computer, desktop computer or the like.

With reference to FIGS. 10 to 14, there will now be described another example of an approach for utilizing the system implemented using the meshing devices approach of the present teachings, this example utilizing END devices.

The device-to-device interaction of the present example is based upon the communication of tokens between any given number of END devices 61, 62 for the purpose of identifying consumers C1, C2 that have consented to or chosen to take part in END device interactions with END devices of other END device consumers via smartphones 65, 66 that can be configured for communication 63, 64 with the END devices, for example using BTLE. In this example, smartphones are discussed but it will be appreciated that another user device with computing capability and a wireless communication capability for communicating with the END device can be used, suitable examples include smartphones, phablets, tablets, laptop computers and netbook computers or the like.

This approach therefore links the END device 61 of a first consumer C1 to the consumer-to-consumer interactions, and indeed may anonymize the consumer-to-consumer interactions such that one consumer knows nothing about the other consumer other than that other consumer's possession of an END device to which his or her own END device can communicate. The END device 61 is enabled for this interaction through an app 69 running on the consumer's smartphone 65 and without an END device the smartphone has no ability to interact with any other consumer's END device or app.

The END device interactions are, once enabled, based upon proximity to other compatible END devices. When two or more compatible END devices come within range of each other, they interact using the device-to device meshed type interactions discussed above.

This therefore enables app behavior that is based upon or links consumers that share the same social circles 60. In this context social circles is defined by entering one-another's proximity, where proximity is defined by the wireless communication range of the meshed-type device-to-device interactions in accordance with the above examples. In some examples, this range may be of the general order of 50 ft, but as will be appreciated this may vary based upon signal propagation conditions in the vicinity of the END devices. This may, for example, facilitate app functionality based upon a number of proximity interactions with other END devices 62 or based upon information relating to a geographic area in which the device-to-device interactions take place. The app 69 can use preference settings for the app 69 and/or for the END device 61, to change the dynamics of the smartphone app 69.

An example of such an app and the device-to-device interactions of an associated END device is now discussed.

As discussed above, the app requires device-to-device interaction of the END device to be enabled for the app to carry out any processing related to consumer-consumer interaction.

The app 69 of the present example provides that an avatar associated with the consumer's END device 61 can compete in a virtual contest with avatars associated with other consumers' END devices 62. Such virtual competition between the avatars allows the avatars to develop and/or gain new virtual abilities that may be utilized by that avatar in future virtual competition with other consumers' END device avatars. Success in such virtual competitions can earn in-app rewards and achievement badges.

In the app 69, 70 of the present example, each consumer C1, C2 is provided with a set of variables with which to configure through interaction 67, 68 with the app 69, 70 an initial state of the avatar associated with their END device 61, 62.

Then, depending on how a consumer C1, C2 configures and uses his or her END device 61, 62, the app 69, 70 adjusts the avatar to customize its competition abilities. In the present example, the competition may take the form of a virtual contest between the avatars such that the profile of the avatar may include one or more attack and/or defense abilities or characteristics. In the present example, the app 69, 70 makes adjustments to the avatar's capabilities in dependence upon usage characteristics of the END device 61, 62. These usage characteristics may include a power setting which can be adjusted to affect the amount of flavor that is present in the aerosol generated by each device activation, and a device activation count previously recorded by the app 69, 70 from the END device 61, 62. How the usage characteristics are adjusted may be based upon usage preferences set by the consumer C1, C2 in the app 69, 70. For example, a consumer with a personal aim to limit their nicotine intake may set a target maximum number of daily device activations and the app may in response thereto provide a penalty to the competition abilities of the avatar if that target is exceeded while providing a bonus to the avatar if the target is not exceeded.

The END device then can be used to access the inter-avatar competition features of the app. When a consumer's END device 61 establishes a mesh-type connection with another consumer's compatible END device 62 within a proximity range 60 to enable such connection, the END device 61 can interact with the other END device 62 and with the consumer's smartphone 65 to provide via the app 69 an option to challenge the avatar associated with the other consumer's END device 62. Likewise, the other consumer's END device 62 through interaction with the first consumer's END device 61 can provide to the other consumer via their smartphone app 70 the option to challenge the first consumer's avatar.

For such a challenge to be made and accepted, the two consumers need have no knowledge of one another and need not interact directly in the real world.

Either consumer can then independently of the other consumer decide whether or not to make the challenge that has been made available via the app 69, 70 and if such a challenge is made then a competition between the avatars is resolved. In the context of the fight challenge of the present example, the avatar associated with the consumer that issues a challenge is the attacker and the avatar associated with the other consumer is the defender. Thus if both consumers decide to issue a challenge in response to the option being presented by their respective smartphone app 69, 70 then two inter-avatar competitions ensue, one based on each challenge with the challenger of that competition being the attacker.

The actual avatar-to-avatar interaction is in the present example is not handled through the device-to-device interaction between the END devices 61, 62. Rather, once the END devices 61, 62 have interacted such as to enable the respective apps 69, 70 to provide the challenge option, each app has sufficient information describing the avatar associated with the avatar to be challenged that the challenge interaction is handled through a separate data service.

In the present example, the apps obtain the challenged-avatar profile information necessary to perform the challenge interaction via a cloud service 73. In the present example, the cloud service 73 is implemented using a MBass (mobile backend as a service) structure. Based on the information exchange between the END devices, the app knows enough information to obtain the profile for the challenged avatar from the cloud service 73 in interactions 71, 72 and the app is then able to resolve the results of the competition.

In the present example, the competition result is used by the app to record a win/loss log for the avatar. The competition result is also provided to the cloud service 73 in interactions 71, 72 so that the win/loss result can be passed by the cloud service 73 to the app of the challenged avatar and be noted in the win/loss log for that challenged avatar. In other examples, the win/loss result may be recorded only for the challenging avatar such that the win/loss log of the challenged avatar is unaffected by the challenge results. In further examples, the challenge interaction to determine the competition result may be performed within the cloud service 73, with the result then provided to one or both of the app of the challenging avatar and the challenged avatar.

Figure 11:
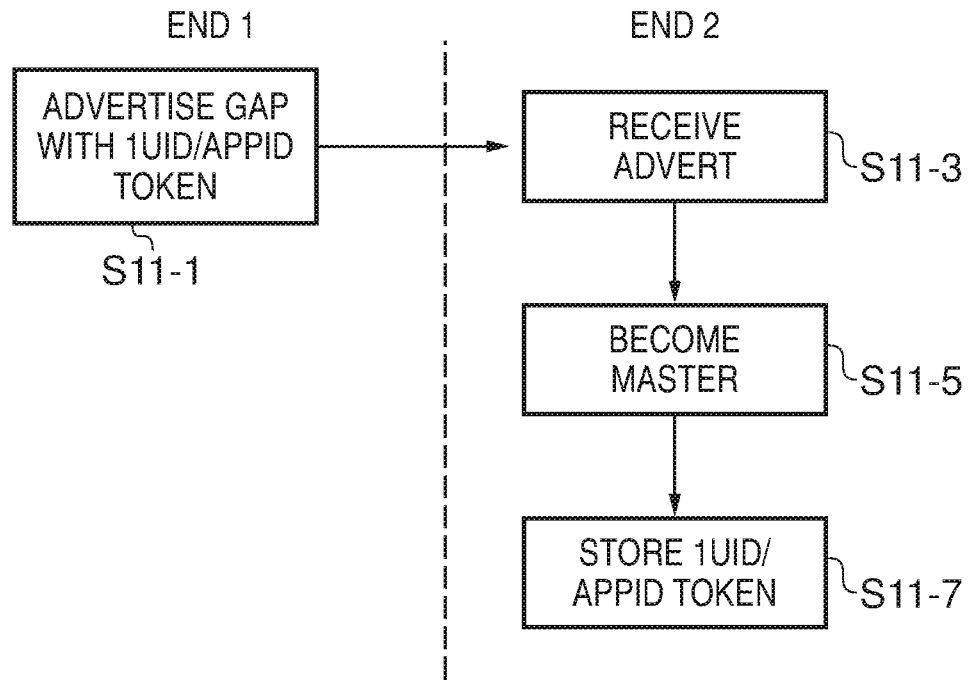
FIG. 11 schematically illustrates an advertising interaction.
Figure 12:
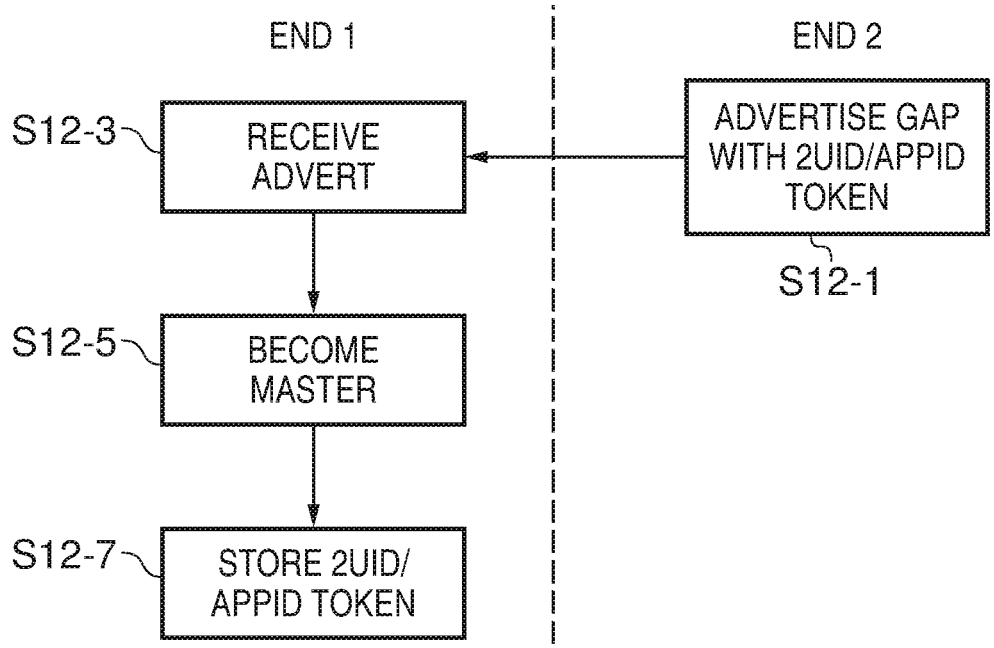
FIG. 12 schematically illustrates an advertising interaction.

The various steps performed by the END devices to provide the device-to-device interaction that underpins performance of the app are illustrated in FIGS. 11 and 12.

FIG. 11 illustrates the process by which a user and app identifier token is passed from the first consumer's END device 61 to a second consumer's END device 62. As illustrated in FIG. 11 the first END device 61, during its window operating in the advertising persona, advertises at S11-1 according to the BTLE GAP with data, the data being in the form of a token including an identifier of the first user and an identifier of the app, 1UID/1APPID. This advertisement is received by the second END device 62 at S11-3. When the second END device 62 receives the advert while it is in its window operating in the observing persona, the second END device then becomes a peripheral (slave) to the first END device's central (master) at S11-5. Thus the second END device 62 can then process the data in the advertising token, and the second END device 62 stores the received data token 1UID/1APPID within its own storage memory at S11-7.

As will be appreciated from the discussion above of devices operable to perform in the mesh-type arrangement, each of the first and second END devices 61 and 62 will each adopt both the advertising and listening personas at different times. Thus, in addition to the method illustrated in FIG. 11 for transfer of data token from the first END device 61 to the second END device 62, the reverse process will also occur when the opposite personas coincide. This is illustrated at S12-1, S12-3, S12-5, and S12-7 in FIG. 12.

Figure 13:
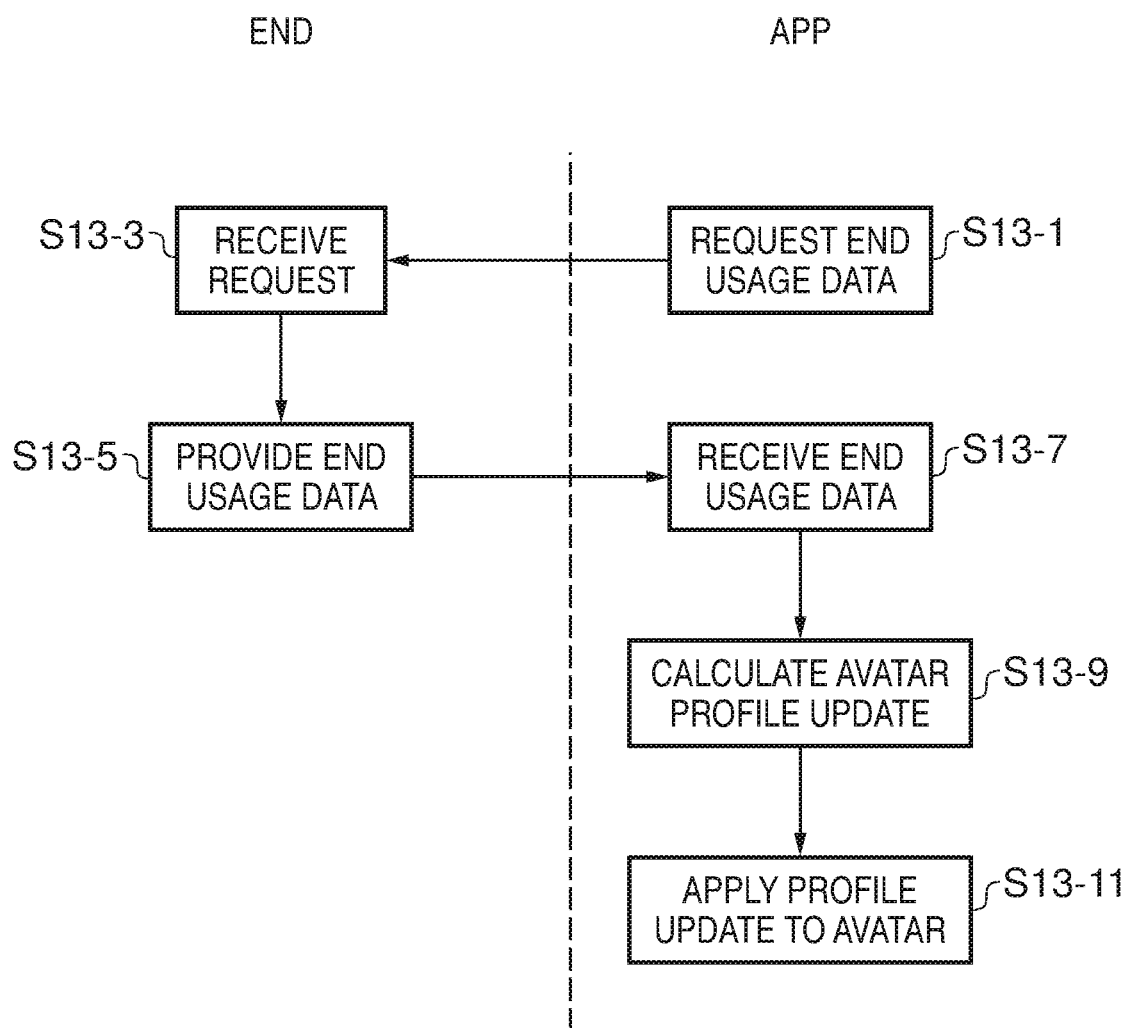
FIG. 13 schematically illustrates an interaction based upon data exchanged via advertising in a meshing approach.

As discussed above, the usage of an END device can be used to modify the profile of an associated user avatar. This process is illustrated in FIG. 13. This process may be followed in order to update the avatar at suitable intervals, which may be defined by rules governing the competition implementation. In some examples, the avatar update may be performed once per day, once per week, multiple times per day or multiple times per week. The update frequency may be user configurable and/or may be related to the nature of one or more usage targets.

In the following discussion, this process will be described with respect to the first END device 61 interacting with the app 69 of the first smartphone 65. It will be appreciated that the same approach can be used for communication between the second END device 62 and the second app 70 of the second smartphone 66.

The update process starts at S13-1 with the app 69 sending a request to the END device 61 for the END device 61 to provide usage data. Upon receipt of this request by the END device 61 at S13-3, the END device 61 then at S13-5 provides the usage data to the app 69. The app 69 receives the usage data at S13-7 and then uses this at S13-9 to calculate any modifications to the avatar profile that result from the usage data. For example, in the context of the present example where competition between avatars is in the form of a virtual fight based upon attack and defense characteristics, failure to meet a defined usage target may result in the avatar profile having one or both of the attack and defense characteristics reduced. Alternatively, or in addition, an attack and/or defense ability or bonus may be reduced or deactivated. On the other hand, if a usage target has been met, then the avatar profile may have one or both of the attack and defense characteristics increased. Alternatively, or in addition, an attack and/or defense ability or bonus may be increased or activated.

Once the avatar update has been determined, the updated avatar profile is then stored at S13-11. Subsequent to this process, for example at a next connection time between the app and the cloud service, or as a final (not shown) step in the process of FIG. 13, the app can transmit the updated avatar profile to the cloud service for storage by the cloud service. The cloud service will then be able to provide the up-to-date avatar profile to another instance of the app for use in defending against a challenge from that user's avatar.

Figure 14:
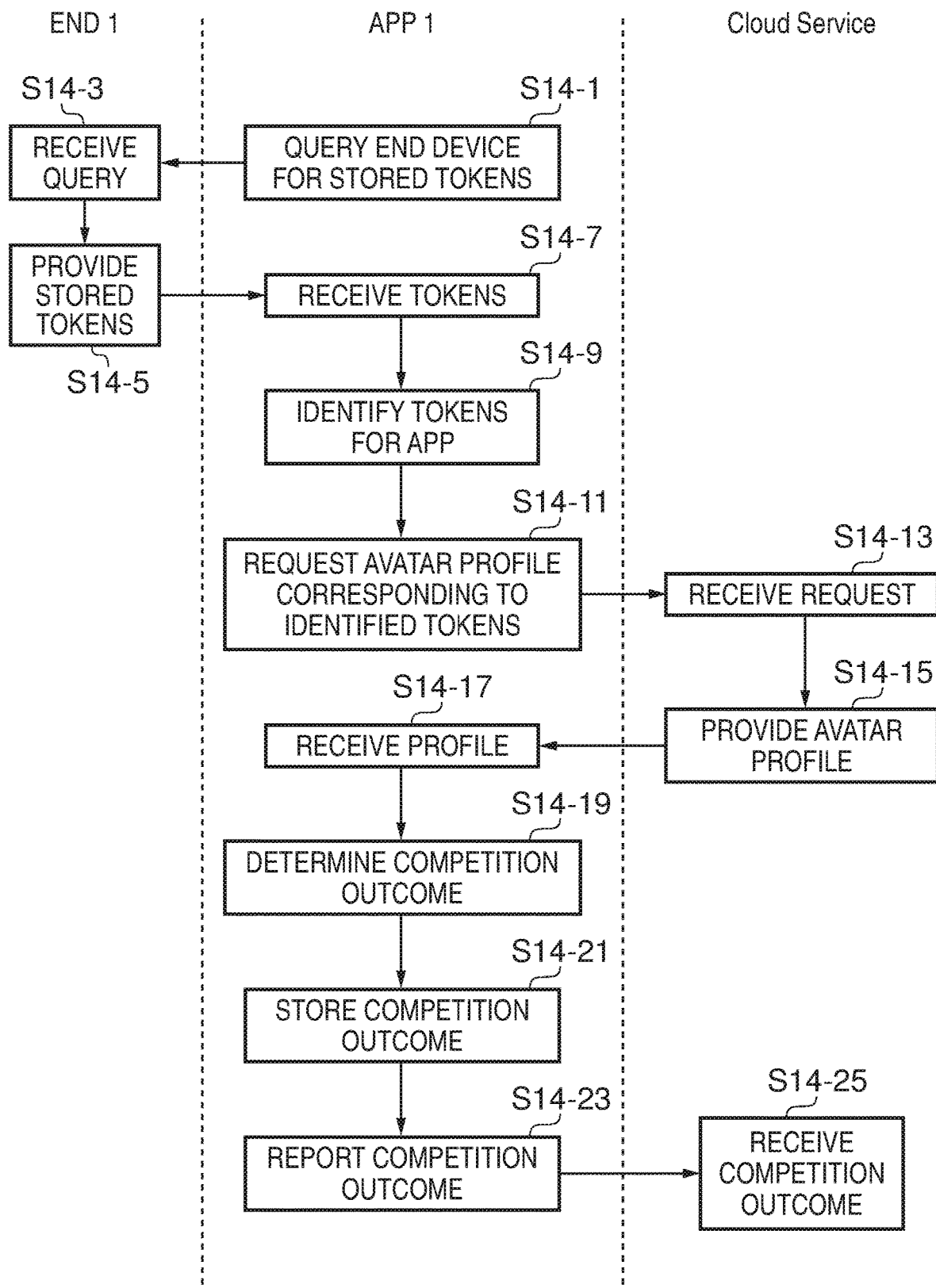
FIG. 14 schematically illustrates an interaction based upon data exchanged via advertising in a meshing approach.

Subsequent to any END device to END device interaction as described with reference to FIGS. 11 and 12 above, each END device can pass on any advertising tokens that it has received to the app at the respective user's smartphone. This process is illustrated in FIG. 14. In the following discussion, this process will be described with respect to the first END device 61 interacting with the app 69 of the first smartphone 65. It will be appreciated that the same approach can be used for communication between the second END device 62 and the second app 70 of the second smartphone 66.

Referring to FIG. 14, at S14-1, the app 69 sends a query for stored tokens to the first END device 61. The END device 61 receives this query at S14-3 and then provides the stored tokens to the app at S14-5. The app 69 receives the tokens from the END device 61 at S14-7 and at S14-9 identifies from the received tokens those which are relevant to that app.

As an alternative, instead of the app associated with the avatar and challenge activity retrieving tokens from the END device, a END device management app of the smartphone could retrieve tokens for the END device and then make the relevant tokens available to the app associated with the avatar and challenge activity.

Having identified at least one relevant token received from the END device 61, the app 69 then requests at S14-11 from the cloud service 73 the avatar profiles associated with those tokens. At S14-13 the cloud service receives the request and then at S14-15 provides the relevant avatar profiles to the app. Once the app 69 has received the profile(s) corresponding to the at least one token at S14-17, the app 69 then determines the competition outcome at S14-19.

The competition outcome is determined according to the challenge rules defined in the app 69. As discussed above, in the present example the competition may take the form of a virtual fight between the avatars based upon respective attack and defense abilities or characteristics. Thus, for example, the fight may be calculated according to a comparison between an attack characteristic of the challenger avatar and a defense characteristic of the challenged avatar. To provide an element of chance into the fight calculation, a randomly determined modifier in a, for example, 1-20% or 1-15% range may be applied to each characteristic value. Also, or alternatively, the avatar may have a bonus ability or benefit applied based upon the usage information used to modify the profile as discussed above. As an example, where a target usage has been achieved, a bonus ability to double the random factor of the avatar, or to halve the random factor of the opposing avatar may be used.

With the competition outcome determined, the competition outcome is stored by the app 69 at S14-21. The competition outcome is also reported to the cloud service at S14-23, which report is received by the cloud service for association with the respective avatar profile at S14-25.

Thus each app 69, 70 can interact with the cloud service to initiate challenge competitions and to receive results of challenge competitions, whether initiated by or against the avatar associate with the owner or user of the smartphone on which the app is running.

The outcome of the competition is thus calculated by the app of the user making the challenge based upon an avatar profile for the challenged avatar provided by the cloud service in response to a request based on that challenged avatar's token. The outcome of the competition will depend on the abilities and/or characteristics of the avatars coupled with one or more random or partially random factors.

The outcome of the competition between two avatars can be seen by the users associated with each of the avatars by accessing the result data as stored on at the cloud service.

In addition to avatar profile improvements and/or bonuses (and the negative equivalents) caused by the END device usage, the avatar profile may also be modified over time as a result of the win/loss outcomes of inter-avatar competition. Win results may be rewarded with points, which can be exchanged for avatar competition abilities and/or for other avatar customizations, such as updates to the appearance of the avatar when displayed on the screen of a smartphone by a relevant app.

The win/loss record of an avatar may also result in recognition tokens or badges being earned by the avatar. For example recognition could be given for winning streaks or other victory patterns. Such recognition badges could be displayed as a part of a public profile of the avatar via the could service and/or made visible to any potential challenger.

As will be appreciated from the discussion above, while the interactions could take place in real time, such that the competition is resolved as soon as the END tokens have been exchanged by the END devices, it is also possible for challenges to be resolved at a later time convenient to a user and/or on a fixed timescale such as where all exchanged tokens from a particular day are then administered for batch-handling of challenges once per day (or other suitable time interval), and/or administered to permit challenges to be resolved using a turn-based session.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the disclosure scope defined by the claims or limitations on equivalents to the claims, and that other embodiments may be utilized and modifications may be made without departing from the scope and/or spirit of the claims.

Further examples consistent with the present teachings are set out in the following numbered clauses:

[Clause 1] A wireless communication module, comprising: a wireless communication interface configured to operate at different times as a master device and as a slave device in separate communication relationships using the same communication protocol, wherein the interface is configured to switch back and forth between a master device mode and a slave device mode.

[Clause 2] The wireless communication module of clause 1, wherein the wireless communication interface is configured to operate a personal area network protocol.

[Clause 3] The wireless communication module of clause 1 or 2, wherein the wireless communication interface is configured to adopt a communication schedule comprising: during a listening period listening in the master device mode for advertising data transmitted from another wireless communication module operating in the slave device mode; and during an advertising period transmitting in the slave device mode during an advertising period advertising data for transfer to another wireless communication module operating in the master device mode.

[Clause 4] The wireless communication module of clause 1, 2 or 3 wherein the interface is configured to switch between the master device mode and the slave device mode with a variable switching rate such that the interval between subsequent listening periods in at least one of the master device mode and the slave device mode varies.

[Clause 5] The wireless communication module of any preceding clause, wherein the wireless communication interface is configured to operate in the radio frequency band from 2.4 to 2.485 GHz.

[Clause 6] The wireless communication module of any preceding clause, wherein the wireless communication interface is a Bluetooth communication interface.

[Clause 7] The wireless communication module of any preceding clause, wherein the wireless communication interface is a Bluetooth low energy communication interface.

[Clause 8] The wireless communication module of clause 7, wherein the Bluetooth low energy communication interface is configured to operate as a central device when operating as a master device and to operate as a peripheral device when operating as a slave device.

[Clause 9] The wireless communication module of any preceding clause, wherein the wireless communication interface is configured to interleave periods of advertising as a potential master device with periods of observing as a potential slave device.

[Clause 10] A wireless communication network comprising: a first wireless communication module according to any preceding claim; and a second wireless communication module according to any preceding claim; wherein the first module operating in the slave device mode transmits advertising data representative of a data token to be transmitted across the network and the second module operating in the master device mode receives the advertising data transmitted by the first module, thereby to receive the data token; and wherein the second module operating in the slave device mode transmits advertising data representative of a data token to be transmitted across the network and the first module operating in the master device mode receives the advertising data transmitted by the second module, thereby to receive the data token.

[Clause 11] The wireless communication network of clause 10, further comprising: a third wireless communication module according to any of clause 1 to 9; wherein the third module operating in the slave mode transmits advertising data indicative of a data token to be transmitted across the network and the first and second modules operating in the master device mode receive the advertising data transmitted by the third module, thereby to receive the data token; and wherein the third module operating in the master device mode receives advertising data representative of a data token to be transmitted across the network transmitted by the first module and/or the second module operating in the master device mode, thereby to receive the data token.

[Clause 12] The wireless communication network of clause 10 or 11, wherein the first and second modules establish a bond relationship for transmission of data other than the data token therebetween.

[Clause 13] The wireless communication network of clause 10, 11 or 12, wherein the first module additionally participates in a bond relationship with a further wireless communication module using the communication protocol, the further module being configured as a master device of the bond relationship and the first module being configured as a slave device of the bond relationship.

[Clause 14] A method of transmitting data through a mesh network, the method comprising: at a first node of the mesh network adopting an advertising state in which a data token is included in first node advertising data transmitted by the first node; at a second node within wireless communication range of the first node and simultaneously with at least a portion of the duration of the advertising state at the first node, adopting a listening state in which the first node advertising data is received by the second node; at the second node and subsequent to receiving the first node advertising data, adopting an advertising state in which the data token received in the first node advertising data is included in second node advertising data transmitted by the second node.

[Clause 15] The method of clause 14, further comprising: at a third node within wireless communication range of the second node and simultaneously with at least a portion of the duration of the advertising state at the second node, adopting a listening state in which the second node advertising data is received by the third node.

[Clause 16] The method of clause 15, wherein the first and third nodes are different nodes.

[Clause 17] The method of clause 14, 15 or 16, wherein the second node switches back and forth between the advertising state and the listening state.

[Clause 18] The method of clause 17, wherein the duration of the at least one of the advertising and listening states is varied between subsequent adoptions of that state.

[Clause 19] The method of any of clauses 14 to 18, wherein the listening state corresponds to a Bluetooth master mode or a Bluetooth low energy central mode, and wherein the advertising state corresponds to a Bluetooth slave mode or a Bluetooth low energy peripheral mode.

[Clause 20] The method of any of clauses 14 to 19, wherein the duration of the listening state is in the range of 0.01 ms to 5 s.

[Clause 21] The method of any of clauses 14 to 20, further comprising establishing a bond relationship between the first and second nodes.

[Clause 22] The method of any of clauses 14 to 21, wherein at least one node comprises the wireless communication module of any of clauses 1 to 9.

Various embodiments of the claimed scope may suitably comprise, consist of, or consist essentially of, appropriate combinations of the disclosed elements, components, features, parts, steps, means, etc, other than those specifically described herein. In addition, this disclosure may include other concepts not presently claimed, but which may be claimed in future either in combination with or separately to the presently claimed features.

The invention claimed is:

1. A method comprising:
passing a data token from a first wirelessly connectable electronic nicotine delivery (END) device to a second wirelessly connectable END device, wherein the first wirelessly connectable END device passes the data token to the second wirelessly connectable END device by the first wirelessly connectable END device adopting an advertising mode and including the data token in advertising data while the second wirelessly connectable END device is in a listening mode in which the second wirelessly connectable END device can receive advertising data, the second wirelessly connectable END device being configured to switch back and forth between a first persona corresponding to an advertising mode and a second persona corresponding to a listening mode according to a switching schedule that alternates between periods for each of the first and second personas, such that at any one time the second wirelessly connectable END device adopts only one persona; and
using the data token to control an aspect of operation of a third wirelessly connectable device, the third wirelessly connectable device having an established communications relationship with the second wirelessly connectable END device.

2. The method of claim 1, wherein the using the data token to control an aspect of the operation of the third wirelessly connectable device comprises using the data token as an input for an application running on the third wirelessly connectable device.

3. The method of claim 1, wherein the first and second wireless connectable END devices pass the data token using a communication protocol based on a Bluetooth operating standard.

4. The method of claim 1, wherein the first and second wirelessly connectable END devices comprise aerosol delivery devices.

5. The method of claim 1, further comprising the third wirelessly connectable device establishing a benefit to be received by a user as a result of receiving the data token.

6. The method of claim 5, wherein the establishing a benefit comprises: responsive to receiving the data token, transmitting a message to a remote service; and receiving a response from the remote service, the response providing information for determination of a benefit.

7. The method of claim 6, wherein the information for determination of a benefit comprises further data to control an aspect of the operation of the third wirelessly connectable device, the controlled aspect of operation comprising a benefit calculation process.

8. The method of claim 7, wherein the aspect of the operation of a third wirelessly connectable device comprises an inter-user interaction of data associated with a user account.

9. The method of claim 8, wherein the inter-user interaction is a competitive interaction, wherein a result of the inter-user interaction depends in part upon the data token, and wherein the benefit to be received by a user as a result of receiving the data token affects inputs to the competitive interaction.

10. A method of operating a nicotine aerosol provision device, the method comprising:
operating a wireless communication interface of the nicotine aerosol provision device according to a switching schedule which controls switching the wireless communication interface back and forth between a first persona corresponding to an advertising mode and a second persona corresponding to a listening mode, such that at any one time the nicotine aerosol provision device adopts only one persona;
during operation of the listening mode, receiving a data token from a wireless communication interface of another aerosol provision device;
storing the received data token at the nicotine aerosol provision device; and
providing the stored data token to an application operating device for control of an aspect of operation of the application operating device.

11. The method of claim 10, further comprising:
operating the wireless communication interface of the nicotine aerosol provision device in the advertising mode; and
during operation of the advertising mode, transmitting a data token from the wireless communication interface of the nicotine aerosol provision device, the transmitted data token operable to control an aspect of operation of an application operating device associated with another aerosol provision device.

12. A nicotine aerosol delivery device comprising:
a wireless communication interface operable according to a switching schedule which controls switching the wireless communication interface back and forth between a first persona corresponding to an advertising mode and a second persona corresponding to a listening mode, such that at any one time the nicotine aerosol delivery device adopts only one persona, and operable during operation in the listening mode to receive a data token from a wireless communication interface of another aerosol provision device; and
a data store operable to store the received data token;
the wireless communication interface further operable to transmit the received data token to an application operating device having an operational association with the nicotine aerosol delivery device, for control of an aspect of operation of the application operating device.

13. A method comprising:
requesting from a wirelessly connected electronic nicotine delivery (END) device a token stored at the wirelessly connected END device as a result of device-to-device interaction between the wirelessly connected END device and another END device;
receiving the requested token from the wirelessly connected END device;
providing the received token to a remote service;
receiving a profile from the remote service; and
performing a comparison or interaction between the received profile and a profile associated with the wirelessly connected END device.

14. The method of claim 13, further comprising, after receiving the requested token from the wirelessly connected END device, providing a user notification relating to the received token and requesting a user input relating to whether or not to perform the comparison or interaction.

15. The method of claim 13, further comprising providing a request for user input to define a profile associated with the wirelessly connected END device.

16. The method of claim 13, wherein the wirelessly connected END device is wirelessly connected via a personal area network protocol.

17. The method of claim 13, wherein the token is stored at the wirelessly connected END device as a result of device-to-device interaction between the wirelessly connected END device and the another END device using a master/slave protocol in which each of the wirelessly connected END device and the another END device are configured to operate at different times as a master device and as a slave device in separate communication interactions using the same communication protocol, wherein each of the wirelessly connected END device and the another END device are configured to switch back and forth between a master device mode and a slave device mode.

18. The method of claim 13, wherein the performing a comparison or interaction further comprises applying one or more modifiers to one of the profiles.

19. The method of claim 13, wherein the performing a comparison or interaction comprises performing a competitive analysis between the profiles to determine a success result.

20. The method of claim 13, further comprising providing a result of the comparison or interaction to the remote service.

21. The method of claim 13, further comprising querying the wirelessly connected END device for usage information thereof, receiving usage information from the wirelessly connected END device, and modifying the profile associated with the wirelessly connected END device in dependence upon the received usage information.

* * * * *